United States Patent
Mukhopadhyay

(10) Patent No.: US 7,285,261 B2
(45) Date of Patent: Oct. 23, 2007

(54) PREPARATION AND APPLICATION OF NOVEL CHROMIUM BASED NANOCATALYST FOR GAS-PHASE FLUORINATION AND HYDROFLUORINATION REACTIONS

(75) Inventor: Sudip Mukhopadhyay, Buffalo, NY (US)

(73) Assignee: Honeywell International Inc, Morristown, NJ (US)

( * ) Notice: Subject to any disclaimer, the term of this patent is extended or adjusted under 35 U.S.C. 154(b) by 0 days.

(21) Appl. No.: 11/261,305

(22) Filed: Oct. 28, 2005

(65) Prior Publication Data

US 2007/0100172 A1    May 3, 2007

(51) Int. Cl.
*C01F 11/00* (2006.01)
*C01F 5/00* (2006.01)
*C01G 55/00* (2006.01)
*C01G 37/00* (2006.01)
*C01G 31/00* (2006.01)
*C01G 39/00* (2006.01)
*C01G 25/00* (2006.01)

(52) U.S. Cl. .............. 423/592.1; 423/594.17; 423/606; 423/607; 423/608; 423/636; 423/639; 977/811

(58) Field of Classification Search ............. 423/592.1, 423/607, 594.17, 606, 608, 636, 639; 977/811
See application file for complete search history.

(56) References Cited

U.S. PATENT DOCUMENTS

| | | | |
|---|---|---|---|
| 2,917,559 A | 12/1959 | Sweeney et al. | 260/653.6 |
| 5,036,036 A | 7/1991 | Lerou | 502/317 |
| 5,185,482 A | 2/1993 | Manzer | 570/168 |
| 5,345,016 A | 9/1994 | Manzer | 570/168 |
| 5,741,748 A | 4/1998 | Allen et al. | 502/25 |
| 6,841,706 B1 | 1/2005 | Wilmet et al. | 570/169 |
| 2004/0115124 A1* | 6/2004 | Woo et al. | 423/634 |
| 2006/0133990 A1* | 6/2006 | Hyeon et al. | 423/622 |

FOREIGN PATENT DOCUMENTS

WO    WO99/07470    2/1999

OTHER PUBLICATIONS

Park, et al., "Ultra-large-scale syntheses of monodisperse nanocrystals" Dec. 2004, Nature Materials vol. 3, Letters, pp. 891-895.*

* cited by examiner

*Primary Examiner*—Steven Bos
(74) *Attorney, Agent, or Firm*—Colleen D Szuch

(57) ABSTRACT

A process of reacting a metal chloride, especially chromium (III) chloride, with an alkali metal oleate at a temperature of from about 30° to about 300° C., and especially at about 70±1° C., in a solvent to form a metal oleate complex, especially a chromium-oleate complex, and reacting the complex with oleic acid at a reaction temperature of about 300° C. or above in a solvent having a boiling point of higher than the reaction temperature, and precipitating and isolating metal oxide nanocrystals, especially chromium (III) oxide nanocrystals, which are useful as a catalyst in hydrofluorination reactions. Other metal oxide nanocrystals produced by this process include nanocrystals of vanadium oxide, molybedenum oxide, rhodium oxide, palladium oxide, ruthenium oxide, zirconium oxide, barium oxide, magnesium oxide, and calcium oxide are also synthesized by similar process scheme using their respective chloride precursors. The chromium (III) oxide nanocrystals produced are especially useful as a highly selective catalyst for hydrofluorination of chlorocarbons, hydrochlorocarbons, hydrofluorocarbons, hydrochlorofluorocarbons, chlorofluorocarbons and aliphatic hydrocarbons with HF to produce fluorinated or more highly fluorinated products.

13 Claims, No Drawings

PREPARATION AND APPLICATION OF NOVEL CHROMIUM BASED NANOCATALYST FOR GAS-PHASE FLUORINATION AND HYDROFLUORINATION REACTIONS

FIELD OF THE INVENTION

This invention relates to a method for the simple and inexpensive method for the production of metal oxides, and particularly chromium (III) oxide, $Cr_2O_3$, in nanocrystalline form from their metal chlorides, and the use of such chromium (III) oxide as a highly selective catalyst for hydrofluorination of chlorocarbons, hydrochlorocarbons, hydrofluorocarbons, hydrochlorofluorocarbons, chlorofluorocarbons and aliphatic hydrocarbons with HF to produce fluorinated or more highly fluorinated products. Other metal oxides such as vanadium oxide, molybedenum oxide, rhodium oxide, palladium oxide, ruthenium oxide, zirconium oxide, barium oxide, magnesium oxide, and calcium oxide in nanocrystalline form are also synthesized by similar process scheme using their respective chloride precursors.

BACKGROUND TO THE INVENTION

Chromium (III) oxide is known as a vapor-phase catalyst for the reaction of chlorocarbons, hydrochlorocarbons, hydrofluorocarbons, hydrochlorofluorocarbons, and chlorofluorocarbons with hydrogen fluoride to produce more fluorinated or more highly fluorinated products. The active species is believed to be the fluorinated form of $Cr_2O_3$ such as oxyfluoride which in turn takes part in a halogen exchange reaction with the hydrocarbons or chlorinated hydrocarbons to form fluorinated or more highly fluorinated products. In this reaction the chromium oxyfluoride exchanges it fluoride atom with the chlorine atoms of the reactant to form the fluorinated product and the catalyst then is in a chlorinated form. The chlorinated form of the catalyst is then fluorinated back to its oxyfluoride form by the interaction with HF which is always present in molar excess. It has been discovered that the catalytic activity of chromium (III) oxide as a fluorination catalyst can vary as a function of the process for the preparation of the chromium (III) oxide. It is also understood that the surface area and particle size of the chromium (III) oxide play significant role in its catalytic activity. Additionally, it is also now recognized that it would be desirable that chromium (III) oxide that is highly effective and selective as a fluorination catalyst be available by a process for its production such that it would be relatively inexpensively produced from inexpensive starting materials and be useful as a catalyst, particularly in industrially significant fluorination reactions.

SUMMARY OF THE INVENTION

In accordance with this invention a process for the preparation of metal oxides, and especially chromium (III) oxide, nanocrystals comprises reacting metal chlorides, and especially chromium (III) chloride, with an alkali metal oleate at a temperature of about 30° C. to about 300° C., preferably about 50 to about 150° C., more preferably at a temperature of from about 65° to about 85° C., most preferably 70±1° C., in a solvent, especially a solvent mixture comprising methanol or ethanol with deionized water and hexane, to form a metal-oleate complex, especially a chromium-oleate complex' and then reacting the metal-oleate complex, especially the chromium-oleate complex, with oleic acid at a temperature of about 300° C. or more, preferably about 315° C. or above in a solvent having a boiling point of about 300° C. or more, preferably about 315° C. or more, and precipitating and isolating the resulting metal oxide nanocrystals, especially chromium (III) oxide nanocrystals. The product preferably is in the form of metal oxide nanocrystals, especially chromium (III) oxide nanocrystals, generally having a particle size of from about 5 nm to about 1000 nm, preferably about 10 to about 500 nm, more preferably from about 20 nm to about 250 nm, most preferably of from 30 nm to about 60 nm, and a surface area of from about 10 $m^2$/gm to about 1400 $m^2$/gm, preferably from about 100 to about 1000 $m^2$/gm, more preferably from about 200 to about 500 $m^2$/gm, most preferably from about 350 $m^2$/gm to about 450 $m^2$/gm. The chromium (III) oxide nanocrystals are a highly selective hydrofluorination catalyst and enable the hydrofluorination reactions to be conducted at generally lower temperatures than has generally been known in industrial hydrofluorination reactions. The chromium (III) nanocrystals produced by the synthesis method of this invention can be employed as highly selective hydrofluorination catalyst for vapor phase fluorination of chlorocarbons, hydrochlorocarbons, hydrofluorocarbons, hydrochlorofluorocarbons, chlorofluorocarbons and aliphatic hydrocarbons with HF to produce fluorinated or more highly fluorinated reaction products. The other metal oxide nanocrystals, vanadium oxide, molybedenum oxide, rhodium oxide, palladium oxide, ruthenium oxide, zirconium oxide, barium oxide, magnesium oxide, and calcium oxide have various utilities known in the art for such metal oxides, such as for example, as catalyst, thermal insulators and components for electrical displays.

DETAILED DESCRIPTION OF INVENTION AND PREFERRED EMBODIMENTS

A highly desirable form of metal oxides, especially chromium (III) oxide in the form of nanocrystals, especially chromium (III) oxide nanocrystals, having a particle size of from about 5 nm to about 1000 nm, preferably about 10 to about 500 nm, more preferably from about 20 nm to about 250 nm, most preferably of from 30 nm to about 60 nm, and a surface area of from about 10 $m^2$/gm to about 1400 $m^2$/gm, preferably from about 100 to about 1000 $m^2$/gm, more preferably from about 200 to about 500 $m^2$/gm, most preferably from about 350 $m^2$/gm to about 450 $m^2$/gm is prepared by the reaction of a metal chloride, especially chromium (III) chloride, with an alkali metal oleate at a temperature of about 30° to about 300° C., preferably at a temperature of from about 30° C. to about 300° C., preferably about 50 to about 150° C., more preferably at a temperature of from about 65° to about 85° C., most preferably 70±1° C., in a solvent, especially a solvent mixture comprising methanol or ethanol with deionized water and hexane, to form a metal-oleate complex, especially a chromium-oleate complex, this complex is then reacted with oleic acid to a temperature of about 300° C. or more, preferably about 315° C. or above in a solvent having a boiling point of about 300° C. or more, preferably about 315° C. or more, (i.e., higher than the reaction temperature) and metal oxide nanocrystals, especially chromium (III) oxide nanocrystals, are isolated from the resulting reaction medium, such as by precipitation and centrifugation.

The metal oxide reactant, an especially chromium (III) chloride ($CrCl_3$) reactant, is preferably employed in its hydrated form, e.g., ($CrCl_3.xH_2O$), and particularly as the hexahydrate ($CrCl_3 \cdot 6H_2O$). The alkali metal oleate reactant may be any suitable alkali metal oleate, preferably potassium or sodium oleate and most preferably sodium oleate.

The reaction temperature of the reaction of the chromium chloride with the oleate salt must be controlled to obtain the desired nanocrystal particle size of about 5 nm to about 1000 nm, preferably about 10 to about 500 nm, more preferably from about 20 nm to about 250 nm, most preferably of from 30 nm to about 60 nm, and is to be a temperature of about 30° C. to about 300° C., preferably about 50 to about 150° C., more preferably at a temperature of from about 65° to about 85° C., most preferably 70±1° C. The reaction is preferably conducted over a period of from about 1 to about 20 hours, a period of from about 2 to about 10 hours, more preferably over a period of from about 3 to about 5 hours, most preferably over a period of about 4 hours.

The metal-oleate complex, especially the chromium-oleate complex, formed from the reaction of the metal chloride, especially the chromium chloride, with the alkali metal oleate is then reacted with oleic acid to form the desired nanocrystals of the metal oxide, especially chromium (III) oxide. This reaction is conducted in any suitable solvent having a boiling point of above 300° C., preferably above 315° C., such as for example, hydrocarbon solvents and hydrocarbyl ether solvents, such as, for example, 1-octadecene, 1-hexadecence, octyl ether, 1-eicosene, trioctylamine and the like, preferably 1-octadecene.

The reaction of the metal-oleate complex, especially the chromium-oleate complex, with the oleic acid is conducted preferably by heating the reactants, dissolved in the reaction solvent, to a temperature of about 315° C. or above by way of a constant heating rate of about 5° C./min and then keeping the reaction mixture at the about 315° C. temperature for about 30 minutes or more, after which the reaction mixture is cooled to room temperature and the desired nanocrystals of the metal oxide product, especially the nanocrystals of the chromium (III) oxide product, is isolated by precipitation in a any suitable solvent, such as an alcohol, preferably ethanol, and the nanocrystals separated by any suitable means, preferably by centrifugation.

The nanocrystals thus obtained are then dried by any suitable means, preferably in a suitable reactor, such as a ½ inch (1.27 cm) Monel® reactor, under an inert gas, preferably helium. The nanocrystals are preferably dried by heat at about 150° C. or more for about 8 hrs, at about 250° C. for about 30 minutes, and then calcined at about 300° C. to about 500° C., preferably at about 350° C., for a period of about 30 minutes to about 3 hours, preferably for about 30 minutes.

The surface area of the metal oxide nanocrystals, especially the chromium (III) oxide nanocrystals, produced by the synthesis process of this invention is generally from about 10 $m^2$/gm to about 1400 $m^2$/gm, preferably from about 100 to about 1000 $m^2$/gm, more preferably from about 200 to about 500 $m^2$/gm, most preferably from about 350 $m^2$/gm to about 450 $m^2$/gm, and the particle size of the nanocrystals is generally about 5 nm to about 1000 nm, preferably about 10 to about 500 nm, more preferably from about 20 nm to about 250 nm, most preferably of from 30 nm to about 60 nm.

The chromium (III) oxide nanocrystals, when employed as a hydrofluorination catalyst, are generally pretreated with hydrogen fluoride before being employed in a fluorination reaction. Conditions for such pretreatment are disclosed, for example in International Patent Publication No. WO 99/07470 and U.S. Pat. Nos. 5,185,482 and 5,345,016, the disclosures of which are incorporated herein by reference thereto. It is believed that this pretreatment converts the chromium oxide which is found at the surface to chromium oxyfluoride. This pretreatment is generally carried out in a reactor, usually that which is used for the hydrofluorination reactions according to the invention, by passing hydrogen fluoride over the calcined and dried chromium (III) oxide nanocrystals, so as to saturate the chromium oxide with hydrogen fluoride. This pretreatment usually takes place over a period of time ranging from 15 to 300 minutes at a temperature generally of between about 200° C. and about 700° C. This pretreatment is often useful but is not essential for the satisfactory operation of the process according to the present invention. Generally, for use as a fluorination catalyst, the chromium (III) oxide nanocrystals of this invention are pretreated with hydrogen fluoride (in anhydrous form) to prepare the nanocrystals in the oxyfluoride form. Any suitable pretreatment conditions may be employed, preferably by reaction with anhydrous HF in the presence on anhydrous $N_2$. By anhydrous HF is meant HF containing less than 0.1% water, preferably less than 0.02%, more preferably less than 0.01%, most preferably less than 0.001%. For example, the chromium (III) oxide nanocrystals may be pretreated with anhydrous HF at a rate of about 3 gm/min in the presence of about 20 cc/min anhydrous $N_2$ at about 345° C. for about 4 hours at atmospheric pressure and then at 50 psig (3.515 kg/$cm^2$) pressure for about 2 hours. The chromium (III) oxide nanocrystals can be employed as such or preferably deposited on a support material, such as for example, on activated carbon or charcoal, graphite, alumina, fluorinated alumina and the like.

Another aspect of this invention is a process for the hydrofluorination of aliphatic hydrocarbons and halogenated hydrocarbons by the action of hydrogen fluoride (HF) on an aliphatic hydrocarbon or halogenated hydrocarbon in the presence of such a chromium (III) oxide nanocrystal catalyst. The term "hydrofluorination" is understood to include the addition reaction of hydrogen fluoride to a carbon-carbon double bond and the substitution reaction of a halogen atom, generally chlorine, by a fluorine atom on a saturated hydrocarbon compound. Such hydrofluorination reaction conditions are described in U.S. Pat. Nos. 2,917,559, 5,741,748, as well as in the previously mentioned International Patent Publication No. WO 99/07470 and U.S. Pat. Nos. 5,185,482 and 5,345,016, the disclosures of all five documents being incorporated herein by reference thereto. In the context of the present invention, the hydrofluorination reactions take place under the catalytic action of the catalyst based on chromium (III) oxide nanocrystals, introduced as such into the reaction mixture or fluorinated beforehand by reaction with hydrogen fluoride.

As examples of halogenated alkanes reactants used in the hydrofluorination reaction process according to the invention, there may be mentioned dichloromethane, chlorofluoromethane, chlorodifluoromethane, 1-chloro-1-fluoroethane, 1,1-di-chloro-1-fluoroethane, 1-chloro-1,1-difluoroethane, chlorotetrafluoroethane isomers, dichlorotrifluoroethane isomers, trichlorodifluoroethane isomers, tetrachlorofluoroethane isomers, pentachloroethane and the like, and mixtures thereof.

As examples of halogenated alkenes used in the process according to the invention, there may be mentioned 1,1-dichloroethylene, trichloroethylene, perchloroethylene, vinyl chloride, 3,3,3-trichloroprop-1-ene, 1,1,3-trichloroprop-1-ene, 1,1,3-tetrachlorobut-1-ene, 1,1,1,3-tetrachlorobut-2-ene, 1,1,1,3-tetrachlorobut-3-ene, 1,1,4,4,4-pentachlorobut-1-ene, 1,1,1,3-tetrachloroprop-2-ene, 1,1,3,3-tetrachloroprop-1-ene, 1,1,3,3-tetrachloro-2-methylprop-2- ene, 1,1,1,3-tetrachloro-2-methylprop-2-ene, 1,1,1,3,3-pentachloroprop-2-ene, 3-chloro-1,1,1-trifluoroprop-2-ene and the mixtures of these compounds.

One aspect of this invention is thus to produce, starting from saturated or unsaturated halogenated hydrocarbon reactants, fluorinated or chlorofluorinated alkanes which comprise more fluorine atoms and fewer chlorine atoms than the reactants used. The invention is targeted in particular at the synthesis of fluorinated hydrocarbons, such as in particular difluoromethane, pentafluoroethane, 1,1,1,2-tetrafluoroethane, 1,1,1-trifluoroethane, 1,1-difluoroethane, 2,2-dichloro-1,1,1-trifluoroethane, 1,1,1-trifluoro-2-chloroethane, 1,1,1,3,3-pentafluoropropane, 1,1,1,3,3-pentafluorobutane, 1,1,1,3,3,3-hexafluorobutane, 1,1,1,3,3-pentafluoro-2-methylpropane and 1,1,1,3,3,3-hexafluoropropane.

The hydrofluorination reaction catalyzed with the chromium (III) oxide nanocrystals is carried out in the gas phase. The process according to the present invention may be carried out as a batch or a continuous reaction, but is preferably carried out continuously.

The molar ratio of the hydrogen fluoride to the aliphatic hydrocarbon or halogenated hydrocarbon employed will generally range from 1 to about 100. This molar ratio is preferably in the range of from about 3 to about 50 and, more preferably, in the range of from about 4 to about 20. The hydrogen fluoride is employed in its anhydrous form.

The reaction pressure is not critical. A pressure of between 1 and 20 bars (14.504 psi to 290.08 psi) is usually employed.

The reaction temperature is generally between ambient temperature and 600° C. The reaction temperature is preferably in the range of from about 100° C. to about 500° C. and, more preferably in the range of from about 200° C. to about 450° C.

Generally, the higher the reaction temperature, the greater the HF/halogenated hydrocarbon molar ratio and the longer the contact time, the higher the degree of conversion of the reactants to fluorinated hydrocarbons and the greater the degree of hydrofluorination. The parameters mentioned above can be adjusted so as to obtain the desired product with high selectivity, a high degree of conversion and a high yield.

The unconverted reactants and the intermediate compounds can advantageously be recycled in the hydrofluorination reactor to increase the productivity with respect to the desired fluorinated product.

The hydrofluorination process according to the invention can be carried out in any type of reactor or apparatus which is resistant to pressure, to hydrogen fluoride and to hydrogen chloride and, in the case of a continuous process, which makes it possible to continually maintain a substantially stable composition of the reaction mixture. The process according to the invention is carried out continuously in a gas phase reactor equipped with a device for introducing the reactants, in the liquid or gas phase, and for withdrawing a gas stream, for example in a tubular reactor filled with a stationary catalyst bed.

The optimum residence time, expressed as the ratio of the total throughput of the reactants (at reaction temperature and pressure) to the free volume of the reactor, can generally vary from 5 seconds to 10 minutes.

The invention is illustrated by, but not limited to, the following examples.

Chromium (III) Oxide Nanocrystals Synthesis 10.66 gm (40 mmol) of chromium(III)chloride hexahydrate (Aldrich Chemicals, 99.995% pure) and 36.5 g (125 mmol) of sodium oleate were dissolved in a mixed solvent composed of 80 ml ethanol and 60 ml deionized water and 140 ml hexane. The resulting solution was heated to 70° C. and kept at that temperature for four hours. After 4 hours, the organic layer containing the chromium-oleate complex was washed four times with 15 ml deionized water in a separatory funnel. After washing, the layers were separated and hexane was distilled off from the organic layer, resulting in a chromium-oleate complex.

40 mmol of the freshly prepared chromium-oleate complex and 20 mmol of oleic acid were dissolved in 200 gm of 1-octadecene (bp 317° C.) at room temperature. The reaction mixture was then heated to 315° C. with a constant heating rate of 5° C./min, and then kept at that temperature for 30 min. After that time the resulting solution was cooled to room temperature and 450 ml ethanol was added to the solution to precipitate the nanocrystals. The nanocrystals were separated by centrifugation. Other solvents such as 1-hexadecene (bp 274° C.), octyl ether (bp 287° C.), 1-eicosene (bp 330° C.), and trioctylamine (bp 365° C.) were also used with success in this reaction.

The chromium (III) oxide nanocrystals thus obtained was then charged in a ½ inch Monel® reactor, dried under 20 cc/min He at 150° C. for 8 h, 250° C. for ½ h, and finally calcined at 350° C. for ½ surface area of the catalyst was around 350-450 $m^2$/gm and the particle size was around 50-200 nm.

Vanadium Oxide Nanocrystals Synthesis 8 gm (50 mmol) of Vanadium (III) chloride hexahydrate (Aldrich Chemicals, 99.995% pure) and 36.5 g (125 mmol) of sodium oleate were dissolved in a mixed solvent composed of 80 ml ethanol and 60 ml deionized water and 140 ml hexane. Methanol can also be used as a solvent instead of ethanol. The resulting solution was heated to 70° C. and kept at that temperature for four hours. After 4 hours, the organic layer containing the vanadium-oleate complex was washed four times with 15 ml deionized water in a separatory funnel. After washing, the layers were separated and hexane was distilled off from the organic layer, resulting in vanadium-oleate complex.

40 mmol of the freshly prepared vanadium-oleate complex and 20 mmol of oleic acid were dissolved in 200 gm of 1-octadecene (bp 317° C.) at room temperature. The reaction mixture was then heated to 315° C. with a constant heating rate of 5° C./min, and then kept at that temperature for 30 min. After that time the resulting solution was cooled to room temperature and 450 ml ethanol was added to the solution to precipitate the nanocrystals. The nanocrystals were separated by centrifugation. The particle size of V(III) oxide was 70-150 nm.

Other metal oxides such as molybedenum oxide, rhodium oxide, calcium oxide are also synthesized by similar process scheme using their respective chloride precursors.

For catalytic hydrofluorination reactions, the nanocrystals were pretreated with HF (3 gm/min) in the presence of 20 cc/min of anhydrous $N_2$ at 345° C. for 4 hr at atmospheric pressure and then at 50 psig pressure for 2 hr.

Hydrofluorination Catalysis Example 1

Reaction of Tetrachloroethylene with HF to Pentafluoroethane (R125)

A 22-inch by ¼-inch diameter (55.88 cm by 0.635 cm)) Monel® tube reactor was charged with 10 g of prefluorinated chromium (III) oxide nanocrystals catalyst (about 1.5 wt. % catalyst on activated carbon support). Through a bed of 10 gm of the fluorinated nanocatalyst, 10 gm/min (0.5 mol/min) of HF and 6 gm/min (0.036 mol/min) of tetrachloroethylene with a were passed at 280-350° C. to synthesize 40 mol % of R125 at a organic conversion level of 96%.

In a typical gas-phase reaction, the reactor was mounted inside a heater with three zones (top, middle and bottom). The reactor temperature was read by a custom made 5-point thermocouples kept at the middle inside of the reactor. The inlet of the reactor was connected to a pre-heater, which was kept at 300° C. by electrical heating. The reactor was kept at 350° C. The catalyst was dried at 350° C. for 8 h in the presence of 20 SCCM of anhydrous $N_2$ and then fluorinated with liquid-HF (50 g/h) for 6 h at 350° C. under 25-psig pressure (1.7237 bars). The liquid-HF was fed from a cylinder into the pre-heater through a needle valve, liquid mass-flow meter, and a research control valve at a constant flow. (HF, 1-1000 g/h). The HF cylinder was kept at a constant pressure of 40 psig (2.7579 bars) by applying anhydrous $N_2$ gas pressure into the cylinder head space. A 6 g/h (1-120 g/h) of tetrachloroethylene was fed into the preheater from a cylinder kept under 100 psig (6.8948 bars) of $N_2$ pressure through a needle valve, liquid mass-flowmeter, and a control valve. The molar ratio of HF to organic was 14. All feed cylinders were mounted on scales to monitor their weight by difference. The reactions were run at a constant reactor pressure of 25 psig (1.7237 bars) by controlling the flow of reactor exit gases by another research control valve. The exit gases coming out of the reactor were analyzed by on-line GC and GC/MS connected through a hotbox valve arrangements to prevent condensation. The conversion of tetrachloroethylene was almost 96-100% and the selectivity to R125 was 40-50%. The product was collected by flowing the reactor exit gases through a 20-60 wt % aqueous KOH scrubber solution and then trapping the exit gases from the scrubber into a cylinder kept in dry ice or liquid $N_2$. The products were then isolated by distillation.

Comparative Hydrofluorination Catalysis Examples

Comparative catalysis examples of hydrofluorination of tetrachloroethylene with HF to pentafluoroethane (R125) were rum with the chromium (III) oxide nanocrystals of this invention and with commercially available ⅛ inch (0.318 cm) diameter chromium (III) oxide pellets from Englehard. The comparative catalyst performances are reported in Table 1.

TABLE 1

Comparative Catalyst Performance

| Catalyst | Temp, °C. | Pressure, psig (bars) | Molar ratio of HF to organic | Conversion of tetrachloro-ethylene | Selectivity to R125 |
|---|---|---|---|---|---|
| Commercial —$Cr_2O_3$ | 350 | 25 (1.7237) | 14 | 87 | 21 |
| $Cr_2O_3$—nanocrystals | 350 | 25 (1.7237) | 14 | 100 | 42 |
| Commercial —$Cr_2O_3$ | 320 | 25 (1.7237) | 14 | 72 | 16 |
| $Cr_2O_3$—nanocrystals | 320 | 25 (1.7237) | 14 | 96 | 40 |

Comparative Catalyst Deactivation

The deactivation rate for the chromium (III) oxide nanocrystal catalyst and for the afore-mentioned commercially available ⅛ inch (0.318 cm) diameter chromium (III) oxide pellets from Englehard was also evaluated and the results are reported in Table 2

TABLE 2

Catalyst deactivation study

| Catalyst | Time, hrs | % Deactivation |
|---|---|---|
| Commercial-$Cr_2O_3$ | 100 | 2 |
| $Cr_2O_3$-nanocrystals | 100 | 0 |
| Commercial-$Cr_2O_3$ | 150 | 3 |
| $Cr_2O_3$-nanocrystals | 150 | 0 |

Hydrofluorination Catalysis Example 2

Reaction of Propylene with HF to 2-Fluoropropane

In a gas-phase reaction a Monel® tube reactor was charged with 100 cc of catalyst. The reactor was mounted in a constant temperature sand-bath with 40-50 ml/min of air flowing through the sand-bath. The sand-bath set point was set at 28° C. during the reaction. The inlet of the reactor was connected to a pre-heater which was kept at 106° C. by supplying 30 psig (2.0684 bars) steam through the jacket. The liquid-HF was fed from a cylinder into the pre-heater through a positive displacement pump and kept at a constant flow of 10 g/h (0.5 mol/h) by controlling the flow with a research control valve. The HF cylinder was kept at a constant pressure of 35 psig (2.4132 bars) by applying anhydrous $N_2$ gas pressure into the cylinder head space. A 21 g/h (0.5 mol/h) of propylene is fed as a gas from a cylinder through a regulator, needle valve, and flow controller directly into the reactor inlet at a point just after the pre-heater. HF and propylene cylinders were mounted on two different scales to monitor their weight by difference. The reactions were run at a constant reactor pressure of 25 psig (1.7237 bars) by controlling the flow of reactor exit gases by another research control valve. The mole ratio of HF to Propylene was kept at 1-3. The exit gases coming out of the reactor were analyzed by an on-line GC and GCMS connected through a hotbox valve arrangements to prevent condensation. The conversion of propylene was almost 100% and the selectivity to 2-fluoropropane was 98%. The reaction was performed continuously over 6 days period to test catalyst deactivation. The product mixture was collected by flowing the reactor exit gases through a 20-60 wt % aqueous KOH scrubber solution and then trapping them in a cylinder kept inside dry ice or liquid $N_2$.

Comparative Hydrofluorination Catalysis Examples

Comparative catalysis examples of hydrofluorination of propylene with HF to 2-fluoropropane were rum with the chromium (III) oxide nanocrystals of this invention and with commercially available activated carbon and commercially available $FeCl_3$ usually employed as catalysts for this reaction. The comparative catalyst performances are reported In Table 3.

TABLE 3

Comparative Catalyst performances

| Catalyst | Temp. °C. | Pressure, psig (bars) | Molar ratio of HF to organic | % Conversion of propylene | % Selectivity to 2-Fluoropropane |
|---|---|---|---|---|---|
| Commercial - activated carbon | 30 | 25 (1.7237) | 1 | 79 | 96 (4% Polymer formation) |
| 1-1.5 wt % $Cr_2O_3$— nanocrystals supported on carbon | 30 | 25 (1.7237) | 1 | 94 | 100 (no polymer formation) |
| Commercial - 4-6 wt % $FeCl_3$ on carbon (NORIT RFC 3) | 30 | 25 (1.7237) | 1 | 83 | 98 (2% Polymer formation) |

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

What is claimed is:

1. A process for the preparation of metal oxide nanocrystals, the process comprising reacting a metal chloride with an alkali metal oleate at a temperature of from about 30° to about 300° C. in a solvent to form a metal-oleate complex, and reacting the metal oleate complex with oleic acid at a reaction temperature of about 300° C. or above in a solvent having a boiling point higher than the reaction temperature, and precipitating and isolating the metal oxide nanocrystals, and wherein the metal oxide nanocrystals produced by the process comprise metal oxide nanocrystals selected from the group consisting of chromium oxide, vanadium oxide, molybedenum oxide, rhodium oxide, palladium oxide, ruthenium oxide, zirconium oxide, barium oxide, magnesium oxide, and calcium oxide nanocrystals.

2. A process of claim 1 wherein the solvent for the reaction of the metal chloride with the alkali metal oleate is a solvent mixture of methanol or ethanol with deionized water and hexane.

3. A process according to claim 2 wherein the alkali metal oleate reactant is sodium oleate, and the resulting metal oxide nanocrystals have a particle size of from about 20 nm to about 250 nm and a surface area of from about 350 $m^2$/gm to about 450 $m^2$/gm.

4. A process according to claim 3 wherein the metal oxide nanocrystals are precipitated in ethanol and isolated by centrifugation.

5. A process for the preparation of chromium (III) oxide nanocrystals, the process comprising reacting chromium (III) chloride with an alkali metal oleate at a temperature of from about 30° to about 300° C. in a solvent to form a chromium-oleate complex and reacting said complex with oleic acid at a reaction temperature of 300° C. or above in a solvent having a boiling point ef higher than the reaction temperature, and precipitating and isolating chromium (Ill) oxide nanocrystals.

6. A process according to claim 5 wherein the solvent for the reaction of the chromium chloride with the alkali metal oleate is a solvent mixture of methanol or ethanol with deionized water and hexane.

7. A process according to claim 6 wherein the alkali metal oleate reactant is sodium oleate.

8. A process according to claim 7 wherein the chromium (III) oxide nanocrystals are precipitated in ethanol and isolated by centrifugation.

9. A process according to claim 8 wherein the reaction of the chromium-oleate complex with oleic acid is conducted at about 315° C. by heating the reaction mixture to 315° C. at a constant heating rate of about 5° C./min and then keeping the temperature at 315° C. for about 30 minutes, followed by cooling the reaction mixture to room temperature before the isolation step.

10. A process according to claim 6 wherein the isolated chromium (III) oxide nanocrystals are dried and calcined.

11. A process according to claim 9 wherein the isolated chromium (III) oxide nanocrystals are dried and calcined.

12. A process according to claim 6 wherein the chromium (III) oxide nanocrystal product is nanocrystals that have a particle size of from about 20 nm to about 250 nm and a surface area of from about 350 $m^2$/gm to about 450 $m^2$/gm.

13. A process according to claim 11 wherein the chromium (III) oxide nanocrystal product is nanocrystals that have a particle size of from about 20 nm to about 250 nm and a surface area of from about 350 $m^2$/gm to about 450 $m^2$/gm.

* * * * *